United States Patent
Donnelly

(10) Patent No.: US 8,404,735 B2
(45) Date of Patent: Mar. 26, 2013

(54) PARASITICIDAL FORMULATION

(75) Inventor: Martin Benedict George Donnelly, Nottingham (GB)

(73) Assignees: Omnipharm Limited, Nottingham (GB); Fidopharm, Inc., Yardley, PA (US)

(*) Notice: Subject to any disclaimer, the term of this patent is extended or adjusted under 35 U.S.C. 154(b) by 0 days.

(21) Appl. No.: 13/442,529

(22) Filed: Apr. 9, 2012

(65) Prior Publication Data
US 2012/0196912 A1 Aug. 2, 2012

Related U.S. Application Data

(63) Continuation of application No. 12/727,003, filed on Mar. 18, 2010.

(60) Provisional application No. 61/161,361, filed on Mar. 18, 2009.

(51) Int. Cl.
*A01N 43/56* (2006.01)
*A61K 31/415* (2006.01)

(52) U.S. Cl. .................................................. 514/407

(58) Field of Classification Search .................. None
See application file for complete search history.

(56) References Cited

U.S. PATENT DOCUMENTS

| | | |
|---|---|---|
| 4,166,107 A | 8/1979 | Miller et al. |
| 4,395,407 A | 7/1983 | Ballany et al. |
| 4,607,050 A | 8/1986 | Kieran et al. |
| 4,764,529 A | 8/1988 | Naik et al. |
| 4,804,675 A | 2/1989 | Jensen-Korte et al. |
| 4,973,589 A | 11/1990 | Barnett et al. |
| 5,045,536 A | 9/1991 | Baker |
| 5,053,227 A | 10/1991 | Chiang et al. |
| 5,059,593 A | 10/1991 | Stendel et al. |
| 5,120,716 A | 6/1992 | Miyazawa et al. |
| 5,141,938 A | 8/1992 | Lindner et al. |
| 5,192,787 A | 3/1993 | Bowers et al. |
| 5,194,264 A | 3/1993 | Van Tonder |
| 5,232,940 A | 8/1993 | Hatton et al. |
| 5,256,679 A | 10/1993 | Minamida et al. |
| 5,266,234 A | 11/1993 | Ho et al. |
| 5,439,924 A | 8/1995 | Miller |
| 5,468,765 A | 11/1995 | Banks et al. |
| 5,482,956 A | 1/1996 | Lunkenheimer et al. |
| 5,516,787 A | 5/1996 | Takada |
| 5,567,429 A | 10/1996 | Senbo |
| 5,612,047 A | 3/1997 | Duffy et al. |
| 5,629,334 A | 5/1997 | Takada |
| 5,777,075 A | 7/1998 | Scherkenbeck et al. |
| 5,876,739 A | 3/1999 | Turnblad et al. |
| 5,939,441 A | 8/1999 | Stetter et al. |
| 6,010,710 A | 1/2000 | Etchegaray |
| 6,096,329 A | 8/2000 | Jeannin |
| 6,395,765 B1 | 5/2002 | Etchegaray |
| 6,565,450 B1 | 5/2003 | Nakahara |
| 6,673,836 B2 | 1/2004 | Ramos |
| 6,716,442 B2 | 4/2004 | Hunter et al. |
| 6,828,275 B2 * | 12/2004 | Uhr et al. ............... 504/139 |
| 8,071,116 B2 | 12/2011 | Sirinyan et al. |
| 8,119,150 B2 | 2/2012 | Tamarkin et al. |
| 2002/0064547 A1 | 5/2002 | Chern et al. |
| 2002/0151577 A1 | 10/2002 | Etchegaray |
| 2003/0050327 A1 | 3/2003 | Huet et al. |
| 2003/0166688 A1 | 9/2003 | Soll et al. |
| 2004/0167175 A1 | 8/2004 | Soll et al. |
| 2004/0198676 A1 | 10/2004 | Soll et al. |
| 2005/0192319 A1 | 9/2005 | Boeckh et al. |
| 2008/0003282 A1 | 1/2008 | Soll et al. |
| 2010/0125097 A1 | 5/2010 | Pate et al. |
| 2012/0029043 A1 | 2/2012 | Derrieu |

FOREIGN PATENT DOCUMENTS

| | | |
|---|---|---|
| CA | 1069823 | 1/1980 |
| CN | 101288409 A | 10/2008 |
| CN | 101352168 A | 1/2009 |
| EP | 0051786 A1 | 5/1982 |
| EP | 0137627 A2 | 4/1985 |
| EP | 0045424 B1 | 6/1985 |
| EP | 0120286 B1 | 7/1987 |
| EP | 0234119 A1 | 9/1987 |
| EP | 0271923 A1 | 6/1988 |
| EP | 0295117 A1 | 12/1988 |
| EP | 0432494 A2 | 6/1991 |
| EP | 0500209 A1 | 8/1992 |
| EP | 0516590 A1 | 12/1992 |
| EP | 0234119 B1 | 8/1994 |
| EP | 0682869 A1 | 11/1995 |
| EP | 0295117 B1 | 4/2000 |
| EP | 1449435 A1 | 8/2004 |
| EP | 0682869 B1 | 12/2005 |
| EP | 1130966 B2 | 5/2009 |
| EP | 1484033 B1 | 2/2011 |
| FR | 2713889 | 12/1994 |

(Continued)

OTHER PUBLICATIONS

Donahue, W. A., Jr. et al., "Evaluating a synergized pyrethrin/(S)-methoprene spray against feline flea infestations," Veterinary Medicine, pp. 999-1007 (1992).
Summary of Product Characteristics, "Frontline Combo Spot-On Dog M," AN2218/2007 (Jul. 2, 2008).
Frontline Spray Brochure, "Frontline No Other Flea Treatment Works Like It or Lasts Like It," (Mar. 1996).
Dictionaire Medicaments Veterinaires, 14th edition, pp. 1083, Wolters Kluwer, France (2007).

(Continued)

*Primary Examiner* — Jeffrey S. Lundgren
*Assistant Examiner* — William Lee
(74) *Attorney, Agent, or Firm* — Cooley LLP

(57) ABSTRACT

The present invention provides a parasiticidal formulation comprising: Fipronil, or a veterinarily acceptable derivative thereof; at least one $C_1$-$C_6$ alcohol co-solvent, wherein the total amount of $C_1$-$C_6$ alcohol is up to 8% by weight of the formulation; at least one organic solvent which is not the $C_1$-$C_6$ alcohol co-solvent; and at least one crystallization inhibitor, wherein the total amount of crystallization inhibitor is from 2 to 20% by weight of the formulation. The formulations of the invention have higher flash points than known parasiticidal formulations comprising Fipronil and therefore provide safer formulations for use in the home, storage, manufacture and distribution.

18 Claims, No Drawings

FOREIGN PATENT DOCUMENTS

| | | |
|---|---|---|
| GB | 2334888 A | 9/1999 |
| JP | 4-235104 A | 8/1992 |
| JP | 6-65219 | 3/1994 |
| JP | 7-179307 | 7/1995 |
| NZ | 567277 | 4/2008 |
| WO | WO 87/03781 | 7/1987 |
| WO | WO 90/09738 | 9/1990 |
| WO | WO 91/13545 | 9/1991 |
| WO | WO 93/02058 | 2/1993 |
| WO | WO 93/06089 | 4/1993 |
| WO | WO 93/18010 | 9/1993 |
| WO | WO 93/20799 | 10/1993 |
| WO | WO 94/21606 | 9/1994 |
| WO | WO 94/26113 | 11/1994 |
| WO | WO 95/04746 | 2/1995 |
| WO | WO 95/33380 | 12/1995 |
| WO | WO 96/16544 | 6/1996 |
| WO | WO 98/25466 | 6/1998 |
| WO | WO 00/62610 | 10/2000 |
| WO | WO 01/40446 | 6/2001 |
| WO | WO 2005/074912 | 8/2005 |
| WO | WO 2007/018659 | 2/2007 |
| WO | WO 2010/026370 A1 | 3/2010 |
| ZA | 884179 | 6/1988 |

OTHER PUBLICATIONS

Dictionaire Medicaments Veterinaires, 14th edition, pp. 638-639, Wolters Kluwer, France (2007).

Postal, J-M. R. et al., "Field Efficacy of a Mechanical Pump Spray Formulation Containing 0.25% Fipronil in the Treatment and Control of Flea Infestation and Associated Dermatological Signs in Dogs and Cats," Veterinary Dermatology, 6(3):153-158 (1995).

Olsen, A., "Ovicidal effect on the cat flea, Ctenocephalides felis (bouche), of treating fur of cats and dogs with methoprene," International Pest Control, pp. 10-14 (1985).

Garg, R. C. et al., "Pharmacologic profile of methoprene, an insect growth regulator, in cattle, dogs and cats," Topics in Drug Therapy, Journal of the American Veterinary Medical Association, 194(3): 410-412 (1989).

Walters, K. A., "Mechanisms and Prediction of Nonionic Surfactant Effects on Skin Permeability," In: Pharmaceutical Skin Penetration Enhancement, Walters, K. A. et al., (eds.), Marcel Dekker, Inc., New York, Chapter 5: pp. 113-116, 129-131, 136-139; Chapter 10: pp. 229-242; Chapter 11: pp. 243-267; and Chapter 16: pp. 345-364 (1993).

Summary of Product Characteristics for Vet Kem Dog Spray, date of approval: Apr. 2003.

Fraser, C. M. et al. (eds.), The Merck Veterinary Manual, Seventh Edition, Merck & Co., Inc., Rahway, NJ, pp. 796-797, 1497-1502 (1991).

Tomlin, C. (ed.)., The Pesticide Manual, Incorporating the Agrochemicals Handbook, Tenth Edition, The British Crop Protection Council ,Surrey, The United Kingdom and the Royal Society of Chemistry, Cambridge, The United Kingdom, Foreward and pp. 296, 297, 463, 591-593, 680-682, 860 and 861 (1994).

Jeannin, Ph. et al., "Fipronil: a new insecticide for flea control," Proceedings of the British Small Animal Veterinary Association Congress, Birmingham; B.S.A.V.A., p. 174 (1994).

Panchagnula, R. et al., "Development and evaluation of an intracutaneous depot formulation of corticosteroids using transcutol as a cosolvent: in-vitro, ex-vivo and in-vivo rat studies," J. Pharm. Pharmacol., 43:609-614 (1991).

Hardin, B. D. et al., "Developmental toxicity of four glycol ethers applied cutaneously to rats," Environmental Health Perspectives, 57:69-74 (1984).

Chiang, C-M et al., "Bioavailability assessment of topical delivery systems: effect of vehicle evaporation upon in vitro delivery of minoxidil from solution formulations," International Journal of Pharmaceutics, 55:229-236 (1989).

Hadgraft, J. et al., "Skin penetration enhancement," Journal of Dermatological Treatment, 5:43-47 (1994).

Pellett, M. A. et al., "Effect of supersaturation on membrane transport: 2. piroxicam," International Journal of Pharmaceutics, 111:1-6 (1994).

Grasso, P. et al., "Methods of measuring, and factors affecting, percutaneous adsorption," J. Soc. Cosmet. Chem., 23:481-521 (1972).

Lauer, A. C. et al., "Transfollicular Drug Delivery," Pharmaceutical Research, 12(2):179-186 (1995).

Illel, B. et al., "Follicles Play an Important Role in Percutaneous Adsorption," Journal of Pharmaceutical Sciences, 80(5):424-427 (1991).

Hueber, F. et al., "Role of Transepidermal and Transfollicular Routes in Percutaneous Adsorption of Steroids: In Vitro Studies on Human Skin," Skin Pharmacal., 7:237-244 (1994).

Coldman, M. F. et al., "Enhancement of Percutaneous Adsorption by the Use of Volatile: Nonvolatile Systems as Vehicles," Journal of Pharmaceutical Sciences, 58(9):1098-1102 (1969).

Research Disclosure, "Extended Efficacy Spectrum of Azole Pesticides," No. 380, p. 802 (Dec. 1, 1995).

UK, S., Eur. J. Plant Pathol., 101(1):8 (1995).

Genchi, C. et al., Efficacia del Fipronil in Formulazione Spray (Frontline RM) Nel Trattamento Delle Infestazioni da Pulci e da Zecche nel Cane, Professione Veterinaria, No. i., Supplement, pp. 19-22 (1995).

Postal, J. M. et al., "Efficacia di una formulazione spray a base di fiprinol allo 0,25% nel trattamento e nella prevenzione delle infestazioni da pulci nel cane e nel gatto," Proffisone Veterinaria, 1:17-18 (1995).

Atwell, R. et al., "The Effects of Fipronil on Ixodes Holocyclus on Dogs in Northern NSW," Aust. Vet. Pract. 26(3):155 (1996) abstract.

Cooper, P. R. et al., "Use of fipronil to eliminate recurrent infestation by Trichodectes canis in a pack of bloodhounds," The Veterinary Record, 139(4):95 (1996).

Postal et al., "Efficacy of a 0.25% fipronil based formulation spray in the treatment and prevention of flea infestations of dogs and cats," CABA pp. 17-18 (1900) machine translation attached.

International Search Report for International Application No. PCT/EP2008/061394, mailed Dec. 22, 2009.

International Search Report for International Application No. PCT/FR1996/001521, mailed Jan. 23, 1997.

Freedom of Information Summary, NADA 141-026, Trade Name: Program Suspension, Sponsor: Ciba Animal Health, Ciba-Geigy Corporation, Approval Date: Mar. 28, 1995.

Freedom of Information Summary, NADA 141-035, Trade Name: Program Tablets, Sponsor: Ciba Animal Health, Ciba-Geigy Corporation, Approval Date: Nov. 23, 1994.

Kegley, S. et al., PAN Pesticides Database—Pesticide Products, Product Name on Label: Ovitrol plus ii flea, tick and bot spray, Pesticide Action Network, North America, San Francisco, CA (2007).

Kegley, S. et al., PAN Pesticides Database—Pesticide Products, Product Name on Label: Ovitrol plus complete flea collar for cats and kittens, Pesticide Action Network, North America, San Francisco, CA (2007).

Young, D. R. et al., "Efficacy of fipronil/(S)-methoprene combination spot-on for dogs against shed eggs, emerging and existing adult cat fleas (Ctenocephalides felis, Bouche)," Veterinary Parasitology, 125:397-407 (2004).

Ding, Jie, et al., "Evaluation of Ehtoxynonafluorobutane as a safe and environmentally friendly solvent for chiral normal-phase LC-atmospheric pressure chemical ionization/electrospray ionization-mass spectrometry", Journal of chromatography, 2005, 1076(1-2), 34-43.

Wang, Peng, et al., "Chiral resolution of malathion and fipronil on the amylose derivative chiral stationary phase," Yingon Huaxue, 2006, 23(10), 1170-1172. (English abstract only.).

Wang, Peng, et al., "Effects of alcohols and temperature on the direct chiral resolutions of fipronil, isocarbophos and carfentrazon e-ethyl," Biomedical Chromatography, 2003, 19(6), 454-458.

Ying, Guang-Guo, et al., "Sorption of Fipronil and its metabolites on soils from South Australia," Journal of Environmental Science and Health, Part B: Pesticides, Food Contaminants, and Agricultural Wastes, 2001, B36(5), 545-558.

"Frontline Combo Spot-On Cat," 7 pages, (issued Jan. 29, 2004, revised Dec. 2011).

"Frontline Combo Spot-On Dog M," 6 pages, (issued Jan. 29, 2004, revised May 2011).

"Frontline Spot on Dog 10% w/v Spot on Solution," 7 pages, (first authorized Nov. 27, 2006, revised Mar. 2010).

"Frontline Spot on Cat 10% w/v Spot on Solution," 6 pages, (first authorized Nov. 27, 2006, revised May 2010).

* cited by examiner

PARASITICIDAL FORMULATION

CROSS REFERENCE TO RELATED APPLICATION

This application is a continuation of U.S. patent application Ser. No. 12/727,003, filed Mar. 18, 2010, which claims priority to U.S. Provisional Application No. 61/161,361, filed Mar. 18, 2009, the disclosure of which is herein incorporated by reference for all purposes.

TECHNICAL FIELD

This invention relates to a parasiticidal formulation comprising Fipronil, or a veterinarily acceptable derivative thereof. In particular, it relates to parasiticidal formulations comprising Fipronil having improved safety characteristics compared with known Fipronil formulations.

BACKGROUND ART

EP 295 217 A and EP 352 944 A describe a class of 1-N-arylpyrazole-based insecticides. A particular compound of this class is 5-amino-1-(2,6-dichloro-4-(trifluoromethyl)phenyl)-4-((trifluoromethyl)sulfinyl)-1H-pyrazole-3-carbonitrile, also known as Fipronil. Fipronil has proven to be particularly effective as a parasiticide against crop parasites and against mammal ectoparasites, in particular fleas, ticks, flies and myiases.

Fipronil formulations are disclosed in GB 2 331 242 A, which also discloses the combination of Fipronil with other parasiticides. Furthermore, GB 2 317 264 A discloses Fipronil formulations additionally comprising an IGR (insect growth regulator) compound, e.g. Methoprene.

Parasiticidal formulations comprising Fipronil are marketed for use in the home treatment of domestic 20 pets, e.g. cats and dogs. One such formulation is FRONTLINE® PLUS FOR DOGS.

However, a problem with these known formulations is their relatively low flashpoints, i.e. the lowest temperatures at which they can form an ignitable mixture in air. The Material Safety Data Sheet for the FRONTLINE® PLUS FOR DOGS formulation indicates the flashpoint for this formulation to be 36° C. (97° F.).

A liquid which forms an ignitable mixture at 36° C. presents a safety risk during use in the home, and during manufacture, distribution and storage, because temperatures in many countries exceed this level during summer. There is therefore a need for effective parasiticidal formulations comprising Fipronil which have higher flashpoints, and therefore improved safety profiles, but which still retain parasiticidal efficacy.

Accordingly, the object of the present invention is to provide a parasiticidal formulation comprising Fipronil having improved safety while maintaining parasiticidal efficacy.

DISCLOSURE OF THE INVENTION

The present invention provides a parasiticidal formulation comprising:
Fipronil, or a veterinarily acceptable derivative thereof;
at least one $C_1$-$C_6$ alcohol co-solvent, wherein the total amount of $C_1$-$C_6$ alcohol is up to 8% by weight of the formulation;
at least one organic solvent which is not the $C_1$-$C_6$ alcohol co-solvent; and
at least one crystallisation inhibitor, wherein the total amount of crystallisation inhibitor is from 2 10 to 20% by weight of the formulation.

The parasiticidal formulations of the present invention surprisingly have a flashpoint of greater than 36° C. (97° F.). In particular, formulations of the present invention have been shown to have flashpoints between 47° C. and 52° C. and are therefore safer than the known formulations of the prior art. The formulations of the present invention also retain parasiticidal efficacy.

The present invention further provides the use of a formulation according the present invention as a parasiticide, particularly for controlling parasites on a mammal (e.g. a cat or a dog) in need thereof.

The present invention further provides a process for controlling parasites on mammals in need thereof, in particular cats and dogs, said process comprising treating the mammal by application to the skin of a parasiticidally effective dose of a formulation according to the present invention.

EMBODIMENTS OF THE INVENTION

In one embodiment, the amount of Fipronil, or a veterinarily acceptable derivative thereof, in the formulation is from 5% to 20%, alternatively from 5% to 15%, alternatively from 8% to 12%, alternatively about 10% by weight of the formulation.

The term "veterinarily acceptable derivative" of Fipronil includes any veterinarily acceptable salt, solvate or hydrate of Fipronil. The term "veterinarily acceptable salt" includes a salt prepared from veterinarily acceptable non-toxic acids or bases including inorganic or organic acids and bases.

In one embodiment, the formulation of the present invention comprises an IGR (insect growth regulator) compound, e.g. S-Methoprene. In one embodiment, the amount of S-Methoprene in the formulation is from 5% to 25%, alternatively from 5% to 20%, alternatively from 5% to 15%, alternatively from 8% to 12% by weight of the formulation.

The amount of the at least one $C_1$-$C_6$ alcohol co-solvent in the formulation is up to 8% by weight of the formulation. In one embodiment, the amount of at least one $C_1$-$C_6$ alcohol co-solvent in the formulation is from 2% to 8%, alternatively about 5% by weight of the formulation.

Examples of the $C_1$ to $C_6$ alcohol co-solvent are methanol, ethanol, propanol, isopropanol or butanol, and combinations thereof. In one embodiment, the $C_1$ to $C_6$ alcohol is ethanol.

In one embodiment, the formulation comprises at least one antioxidant. In one embodiment, the amount of antioxidant in the formulation is from 0.005 to 1%, alternatively from 0.01 to 0.05%, alternatively from 0.02 to 0.03%, alternatively about 0.03% by weight of the formulation.

Examples of the antioxidant are butylated hydroxylanisole, butylated hydroxyltoluene, alpha tocopheral, ascorbic acid, ascobyl palmitate, fumeric acid, malic acid, citric acid, sodium ascorbate, sodium metabisulfate, n-propyl gallate, monothioglycerol and combinations thereof. In one embodiment, the antioxidant is butylated hydroxylanisole, butylated hydroxyltoluene or combinations thereof. In one embodiment, the at least one antioxidant consists of butylated hydroxylanisole (e.g. in amount of about 0.02% by weight) and butylated hydroxyltoluene (e.g. in amount of 0.01% by weight).

The amount of the at least one crystallisation inhibitor in the formulation is from 2 to 20% by weight of the formulation. In one embodiment, the amount of crystallisation inhibitor in the formulation is from 4% to 15%, alternatively 6% to 12%, alternatively about 10% by weight of the formulation.

The at least one crystallization inhibitor satisfies the following test having steps (i)-(iii): (i) 0.5 ml of a formulation of the invention comprising the at least one crystallisation inhibitor in an amount of 10% by weight is deposited in an open Petri dish at 20° C.; (ii) the deposited formulation is observed at 20 minute intervals; and (iii) no crystals are observed with the naked eye within 3 hours of depositing the formulation.

Examples of the crystallization inhibitor are polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters, polyoxyethylenated hydrogenated castor oil (e.g. PEG-60 hydrogenated castor oil), lecithin, sodium carboxymethylcellulose, or acrylic derivatives such as methacrylates.

Alternatively, or in addition, the crystallization inhibitor may be an anionic surfactant such as alkaline stearates, in particular sodium, potassium or ammonium stearate; calcium stearate; triethanolamine stearate; sodium abietate; alkyl sulphates, in particular sodium lauryl sulphate and sodium cetyl sulphate; sodium dodecylbenzenesulphonate, sodium dioctylsulphosuccinate; fatty acids, in particular those derived from coconut oil.

Alternatively, or in addition, the crystallization inhibitor may be a cationic surfactant such as water-soluble quaternary ammonium salts such as cetyltrimethylammonium bromide, octadecylamine 5 hydrochloride.

Alternatively, or in addition, the crystallization inhibitor may be a nonionic surfactant such as polyoxyethylenated sorbitan esters, in particular polysorbate 80, polyoxyethylenated alkyl ethers; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide.

Alternatively or in addition, the crystallization inhibitor may be an amphoteric surfactant such as a substituted lauryl compound of betaine.

In one embodiment, the at least one crystallization inhibitor is polyethylene glycol (e.g. polyethylene glycol 1000), polyethylene glycol hydrogenated castor oil (e.g. polyethylene glycol 60 hydrogenated castor oil, e.g. Nikkol HCO 60), or combinations thereof.

In one embodiment, the at least one crystallisation inhibitor consists of two crystallisation inhibitors.

In one embodiment, the at least one crystallization inhibitor is polyethylene glycol (e.g. polyethylene glycol 1000) and polyethylene glycol hydrogenated castor oil (e.g. polyethylene glycol 60 hydrogenated castor oil, e.g. Nikkol HCO 60). In one embodiment, the amount of polyethylene glycol is about 5% by weight of the formulation and the amount of polyethylene glycol hydrogenated castor oil is about 5% by weight of the formulation.

As used herein, "polyethylene glycol" includes combinations of polyethylene glycols having different molecular weights.

The formulation of the invention comprises at least one organic solvent which is not $C_1$-$C_6$ alcohol.

Typically, the total amount of the at least one organic solvent which is not $C_1$-$C_6$ alcohol makes up the balance of the formulation. Examples of the at least one organic solvent which is not $C_1$-$C_6$ alcohol are diethylene glycol monoethyl ether, ethylene glycol monoethyl ether, dipropylene glycol n-butyl ether, dipropylene glycol monomethyl ether, or combinations thereof. In one embodiment, the at least one organic solvent which is not $C_1$-$C_6$ alcohol is diethylene glycol monoethyl ether (e.g. Transcutol P).

In one embodiment, the formulation of the present invention consists of:
  9.7 wt % Fipronil;
  5.0 wt % ethanol;
  0.02 wt % butylated hydroxylanisole;
  0.01 wt % butylated hydroxyltoluene;
  5.0 wt % polyethylene glycol 1000;
  5.0 wt % polyethylene glycol 60 hydrogenated castor oil;
  balance diethylene glycol monoethyl ether.

In another embodiment, the formulation of the present invention consists of
  9.8 wt % Fipronil;
  11.8 wt % S-Methoprene;
  5.0 wt % ethanol;
  0.02 wt % butylated hydroxylanisole;
  0.01 wt % butylated hydroxyltoluene;
  5.0 wt % polyethylene glycol 1000;
  5.0 wt % polyethylene glycol 60 hydrogenated castor oil;
    balance diethylene glycol monoethyl ether.

This formulation is particularly suitable for cats.

In another embodiment, the formulation of the present invention consists of
  9.8 wt % Fipronil;
  8.8 wt % S-Methoprene;
  5.0 wt % ethanol;
  0.02 wt % butylated hydroxylanisole;
  0.01 wt % butylated hydroxyltoluene;
  5.0 wt % polyethylene glycol 1000;
  5.0 wt % polyethylene glycol 60 hydrogenated castor oil;
  balance diethylene glycol monoethyl ether.

This formulation is particularly suitable for dogs.

The formulations of the present invention may be manufactured by mixing the desired components in the desired amounts.

The formulations of the present invention are intended for mammals, in particular cats and dogs, and are generally deposited onto the skin ("spot-on" or "pour-on" application). The deposition is generally a localised application over a surface area of less than 10 $cm^2$, especially of between 5 and 10 $cm^2$, in particular at one point or two points which may be located between the mammal's shoulders. Once deposited, the formulation diffuses over the mammal's body and dries without crystallising or modifying the appearance or feel of the fur.

As mentioned above, the present invention provides a process for controlling parasites on mammals, in particular cats and dogs, said process comprising treating the mammal by application to the skin of parasiticidally effective doses of a formulation according to the present invention.

The object of the application of the formulations of the present invention may be non-therapeutic in that it relates to the cleaning of mammal hairs and skin by elimination of parasites, as well as their residues and dejections. The treated mammals will therefore have hair which is more pleasant to look at and feel.

The object of the application of the formulations of the present invention may be therapeutic if the intention is to treat and prevent parasitoses having pathologic consequences.

The process of the present invention may treat the mammal by local point application to the skin of "spot-on" type. Spot-on formulations are particularly advantageous due to their efficacy, their speed of action and the pleasant appearance of the mammal's fur after application and drying.

The process, formulations and use of the present invention is particularly suitable when the parasites are ectoparasites, in particular ticks or fleas.

Treatment of mammals, in particular cats and dogs, with the formulation of the present invention may be carried out every two or three months.

The treatment may be carried out so as to administer to the mammal a does from 0.1 to 80 mg/kg, alternatively from 1 to 40 mg/kg, alternatively from 1 to 30 mg/kg of the parasiticidal component, wherein the parasiticidal component is either Fipronil or the combination of Fipronil and S-Methoprene when S-Methoprene is present.

It is to be understood that these dosage values are average values which may vary because the formulation will be administered to mammals having relatively different body weights. Consequently, the doses applied may be smaller or larger than the doses provided above.

MODES FOR CARRYING OUT THE INVENTION

The invention is further illustrated by the following examples. It will be appreciated that the examples are for illustrative purposes only and are not intended to limit the invention as described above. Modification of detail may be made without departing from the scope of the invention.

Example 1

A formulation of the following composition is prepared by mixing ingredients in the following amounts:
- 9.7 wt % Fipronil;
- 5.0 wt % ethanol;
- 0.02 wt % butylated hydroxylanisole;
- 0.01 wt % butylated hydroxyltoluene;
- 5.0 wt % polyethylene glycol 1000;
- 5.0 wt % polyethylene glycol 60 hydrogenated castor oil (Nikko HCO 60);
- balance diethylene glycol monoethyl ether (Transcutol P).

Example 2

A formulation of the following composition particularly useful for cats is prepared by mixing ingredients in the following amounts:
- 9.8 wt % Fipronil;
- 11.8 wt % S-Methoprene;
- 5.0 wt % ethanol;
- 0.02 wt % butylated hydroxylanisole;
- 0.01 wt % butylated hydroxyltoluene;
- 5.0 wt % polyethylene glycol 1000;
- 5.0 wt % polyethylene glycol 60 hydrogenated castor oil (Nikkol HCO 60);
- balance diethylene glycol monoethyl ether (Transcutol P).

Example 3

A formulation of the following composition particularly useful for dogs is prepared by mixing ingredients in the following amounts:
- 9.8 wt % Fipronil;
- 8.8 wt % S-Methoprene;
- 5.0 wt % ethanol;
- 0.02 wt % butylated hydroxylanisole;
- 0.01 wt % butylated hydroxyltoluene;
- 5.0 wt % polyethylene glycol 1000;
- 5.0 wt % polyethylene glycol 60 hydrogenated castor oil (Nikkol HCO 60);
- balance diethylene glycol monoethyl ether (Transcutol P).

Example 4

Flash Points

The flashpoints of the compositions of Examples 1-3 were measured and were found to be between 15 47-52° C., some 11-18° C. higher than the flashpoint of the marketed product FRONTLINE® PLUS FOR DOGS.

The formulations of the invention therefore have a reduced propensity to form ignitable mixtures with air. They therefore provide a safer formulation for use, storage, distribution and manufacture.

Example 5

Parasiticidal Activity

The compositions of Examples 1-3 have been shown in trials to have parasiticidal activity.

The invention claimed is:

1. A parasiticidal formulation comprising:
   from about 8% to about 12% by weight Fipronil, or a veterinarily acceptable derivative thereof;
   a C1-C6 alcohol, wherein the total amount of the C1-C6 alcohol is about 5% by weight of the formulation; and
   at least one organic solvent which is not the C1-C6 alcohol.

2. The formulation of claim 1, further comprising at least one crystallization inhibitor, wherein the total amount of the crystallization inhibitor is from 2 to 20% by weight of the formulation.

3. The formulation of claim 1, wherein the Fipronil or a veterinarily acceptable derivative thereof, is Fipronil.

4. The formulation of claim 1, which further comprises S-Methoprene.

5. The formulation of claim 4, wherein the amount of S-Methoprene is from about 5% to about 25% by weight of the formulation.

6. The formulation of claim 2, wherein the at least one crystallization inhibitor is polyethylene glycol, polyethylene glycol hydrogenated castor oil, or combinations thereof.

7. The formulation of claim 6, wherein the at least one crystallization inhibitor is a combination of polyethylene glycol and polyethylene glycol hydrogenated castor oil.

8. The formulation of claim 7, wherein the amount of polyethylene glycol is about 5% by weight of the formulation and the amount of polyethylene glycol hydrogenated castor oil is about 5% by weight of the formulation.

9. The formulation of claim 1, wherein the at least one organic solvent which is not the C1-C6 alcohol is diethylene glycol monoethyl ether, ethylene glycol monoethyl ether, dipropylene glycol n-butyl ether, dipropylene glycol monomethyl ether, or combinations thereof.

10. The formulation of claim 9, wherein the at least one organic solvent which is not the C1-C6 alcohol is diethylene glycol monoethyl ether.

11. A method for controlling parasites on mammals in need thereof, said method comprising treating the mammal by application to the skin of parasiticidally effective dose of a formulation of claim 1.

12. The method of claim 11, wherein the mammal is treated by local point application to the skin of a spot-on formulation of claim 1.

13. The method of claim 11, wherein the parasites are one or more ectoparasites.

14. A parasiticidal formulation consisting of:
   about 9.7 wt % Fipronil;
   about 5.0 wt % ethanol;

about 0.02 wt % butylated hydroxylanisole;
about 0.01 wt % butylated hydroxyltoluene;
about 5.0 wt % polyethylene glycol 1000;
about 5.0 wt % polyethylene glycol 60 hydrogenated castor oil;
balance diethylene glycol monoethyl ether.

15. A parasiticidal formulation consisting of:
about 9.8 wt % Fipronil;
about 11.8 wt % S-Methoprene;
about 5.0 wt % ethanol;
about 0.02 wt % butylated hydroxylanisole;
about 0.01 wt % butylated hydroxyltoluene;
about 5.0 wt % polyethylene glycol 1000;
about 5.0 wt % polyethylene glycol 60 hydrogenated castor oil;
balance diethylene glycol monoethyl ether.

16. A parasiticidal formulation consisting of:
about 9.8 wt % Fipronil;
about 8.8 wt % S-Methoprene;
about 5.0 wt % ethanol;
about 0.02 wt % butylated hydroxylanisole;
about 0.01 wt % butylated hydroxyltoluene;
about 5.0 wt % polyethylene glycol 1000;
about 5.0 wt % polyethylene glycol 60 hydrogenated castor oil;
balance diethylene glycol monoethyl ether.

17. The method of claim 11, wherein the mammals are cats or dogs.

18. The method of claim 13, wherein the one or more ectoparasites are fleas and ticks.

* * * * *